(12) United States Patent
Forsell

(10) Patent No.: US 6,678,561 B2
(45) Date of Patent: Jan. 13, 2004

(54) HEARTBURN AND REFLUX DISEASE TREATMENT APPARATUS

(75) Inventor: Peter Forsell, Menzingen (CH)

(73) Assignee: Surgical Development AG, Baar (CH)

( * ) Notice: Subject to any disclaimer, the term of this patent is extended or adjusted under 35 U.S.C. 154(b) by 181 days.

(21) Appl. No.: 09/893,518

(22) Filed: Jun. 29, 2001

(65) Prior Publication Data

US 2002/0193842 A1 Dec. 19, 2002

(30) Foreign Application Priority Data

May 23, 2001 (SE) .............................................. 0101832
Jun. 28, 2001 (SE) .............................................. 0102314

(51) Int. Cl.[7] .......................... A61N 1/32; A61N 1/36; A61N 1/372
(52) U.S. Cl. ........................................................ 607/40
(58) Field of Search ..................... 607/40–41

(56) References Cited

U.S. PATENT DOCUMENTS

| 5,716,385 | A | * | 2/1998 | Mittal et al. ................... 607/40 |
| 5,836,994 | A | * | 11/1998 | Bourgeois ..................... 607/40 |
| 6,021,352 | A | * | 2/2000 | Christopherson et al. ..... 607/42 |
| 6,097,984 | A | * | 8/2000 | Douglas ....................... 607/40 |
| 6,243,607 | B1 | * | 6/2001 | Mintchev et al. ............. 607/40 |

\* cited by examiner

*Primary Examiner*—Carl Layno
(74) *Attorney, Agent, or Firm*—Nixon & Vanderhye P.C.

(57) ABSTRACT

A heartburn and reflux disease treatment apparatus comprises an electric stimulation device (56) adapted to engage the cardia sphincter (58) of a patient, who suffers from heartburn and reflux disease, and electrically stimulate the cardia sphincter to increase the sphincter tonus, so that the cardia completely closes. A control device (62) is provided for controlling a source of energy (64), which may or may not be implanted, to release electric energy for use in connection with the power of the stimulation device.

151 Claims, 4 Drawing Sheets

HEARTBURN AND REFLUX DISEASE TREATMENT APPARATUS

The present invention relates to a heartburn and reflux disease treatment apparatus Heartburn and reflux disease is a widespread medical problem. This is often due to hiatal hernia, i.e. a portion of the stomach immediately below the gastric fundus slides upwardly through the esophageal hiatus. In consequence, stomach acids and foods are regurgitated into the esophagus.

In the late 1970s a prior art restriction device called Angelchik, according to U.S. Pat. No. 3,875,928, was used to operatively treat heartburn and reflux disease. However, the Angelchik restriction device had a major disadvantage in that it was not possible to adjust the size of the restriction opening after the operation. A further disadvantage was that the restriction device did not satisfactorily protect the esophagus and the surrounding area against injuries due to poor shape of the restriction device. Therefore, operations using the Angelchik stimulation device are no longer practised.

An operation technique, semi-fundoduplicatio, is currently in use for treating heartburn and reflux disease. A most common operation is Nissen semi-fundoduplicatio, in which one takes the fundus of the stomach and makes a three-quarter of a turn around the esophagus and suture between the stomach and esophagus. Although this operation works fairly well it has three main disadvantages. Firstly, most patients' treated in accordance to "ad modum Nissen" lose their ability to belch. Secondly, many of these patients's get dysphagia, i.e. difficulties to swallow after the operation. Thirdly, it is not possible to adjust the food passageway in the esophagus or stomach in any way after the operation. Characteristic for these patients's is the variation of their problems over the day. For example, many patients have difficulties during the night when they lie down because of stomach acid leaking up into the esophagus.

It is an object of the present invention to provide a new convenient heartburn and reflux disease treatment apparatus, the performance of which may be affected by the patient at any time after operation, in particular when various needs arise over the day, so that the patient always is satisfied.

This object is achieved by a heartburn and reflux disease treatment apparatus, which is characterised by an implantable electric stimulation device adapted to engage with the cardia sphincter of a patient, who suffers from heartburn and reflux disease, and electrically stimulate the cardia sphincter to increase the sphincter tonus, so that the cardia completely closes. (The term "patient" includes an animal or a human being.

The apparatus preferably comprises a source of energy and a control device controllable from outside the patient's body for controlling the source of energy to release energy for use in connection with the power of the stimulation device, when the stimulation device is implanted. As a result, the apparatus of the invention provides a simple and effective control of the energy supplied to implanted components of the apparatus which ensures an extended and reliable functionality of the apparatus, possibly for the rest of the patient's life and at least many years.

An important problem is that the voltage intensity strong enough to provide the desired stimulation of the cardia sphincter might fade over time, due to increasing electric resistance caused by the formation of fibrosis where the conductors engage the cardia sphincter. This problem is solved by a main embodiment of the present invention, in which the electric source of energy provides a current through the electric conductors. More particularly, the control device is adapted to control the electric source of energy to release electric energy such that the intensity of the current through the electric conductors amounts to a predetermined value. As a result, decreasing current intensity caused by the formation of fibrosis where the conductors engage the cardia sphincter can be compensated for. Thus, if the current through the conductors decreases the control device automatically controls the electric source of energy to release more electric energy to restore the desired current intensity.

Advantageously, the control device is adapted to control the electric source of energy to release energy in the form of an alternating current. The inventor has found that unlike an alternating current a direct current could cause electrolysis in the cardia sphincter. Such electrolysis could injure the cardia sphincter.

The control device may also control the stimulation device.

In accordance with a preferred embodiment of the invention, the source of energy comprises an electric source of energy and the control device is adapted to supply the stimulation device with electric energy from the electric source of energy. In the preferred embodiment, the control device is adapted to control the stimulation device to vary the intensity of the electric stimulation of the cardia sphincter over time. Preferably, the control device is controllable from outside the patient's body to control the stimulation device to change the intensity of the electric stimulation of the cardia sphincter so that the cardia sphincter tonus is changed.

All of the above embodiments may be combined with at least one implantable sensor for sensing at least one physical parameter of the patient, wherein the control device may control the stimulation device in response to signals from the sensor. In particular, the sensor may sense as the physical parameter the contraction wave in the esophagus caused by the patient swallowing food. In this case the electric stimulation device is adapted to cease the stimulation of the cardia sphincter in response to the sensor sensing the contraction wave in the patient's esophagus.

As an alternative, the sensor may comprise a pressure sensor for directly or indirectly sensing the pressure in the esophagus. The expression "indirectly sensing the pressure in the esophagus" should be understood to encompass the cases where the sensor senses the pressure against the stimulation device or human tissue of the patient.

The control device may comprise an internal control unit, preferably including a microprocessor, to be implanted in the patient for controlling the stimulation device. The internal control unit may suitably directly control the stimulation device in response to signals from the sensor. In response to signals from the sensor, for example pressure, the patient's position, the contraction wave in the patient's esophagus or any other important physical parameter, the internal control unit may send information thereon to outside the patient's body. The control unit may also automatically control the stimulation device in response to signals from the sensor. For example, the control unit may control the stimulation device to efficiently stimulate the cardia sphinter, such that the cardia for certain is completely closed in response to the sensor sensing that the patient is lying.

The control device may also, or alternatively, comprise an external control unit outside the patient's body, wherein the internal control unit is programmable by the external control unit, for example for controlling the stimulation device over time. Alternatively, the internal control unit may control the stimulation device over time in accordance with an activity schedule program, which may be adapted to the patient's needs.

The external control unit may also, suitably directly, control the stimulation device in response to signals from the sensor. The external control unit may store information on the physical parameter sensed by the sensor and may be manually operated to control the stimulation device based on the stored information. In addition, there may be at least one implantable sender for sending information on the physical parameter sensed by the sensor.

A great advantage is that the patient is enabled to keep the cardia completely closed by means of the stimulation device by using the control device whenever he likes during the day. This advantage should not be underestimated, because in case the patient would need to vomit it would be very difficult for him to do so if he were unable to immediately stop the electric stimulation of the cardia.

Conveniently, the external control unit may load the internal control unit with data in accordance with a loading mode only authorised for a doctor. For specialised controls of the stimulation device, such as electric power, electric pulse frequency etc, the external control unit may control the internal control unit in accordance with a doctor mode only authorised for the doctor. For simple controls of the stimulation device, such as on and off, the external control unit may control the internal control unit in accordance with a patient mode permitted for the patient. Thus, by using the external control unit in accordance with different modes it is possible to have certain functions of the stimulation device controlled by the patient and other more advanced functions controlled by the doctor, which enables a flexible post-operation treatment of the patient.

The control device may be adapted to control the source of energy to release energy, for instance to intermittently release energy in the form of a train of energy pulses, for direct use in connection with the power of the stimulation device. In accordance with a suitable embodiment the control device controls the source of energy to release electric energy, and the apparatus further comprises an implantable capacitor for producing the train of energy pulses from the released energy. In this case the term "direct" is used to mean, on one hand, that the released energy is used while it is being released by the control device, on the other hand, that the released energy may be somewhat delayed, in the order of seconds, by for instance an energy stabiliser before being used in connection with the power of the stimulation device.

In accordance with an embodiment of the invention, the apparatus comprises implantable electrical components including at least one, or only one single voltage level guard and a capacitor or accumulator, wherein the charge and discharge of the capacitor or accumulator is controlled by use of the voltage level guard.

In accordance with a first main aspect of the invention, the source of energy is external to the patient's body and the control device controls the source of energy to release wireless energy. An energy storage device, preferably an electric accumulator, may be implanted in the patient for storing the wireless energy released from the external source of energy. The electric accumulator may comprise at least one capacitor or at least one rechargeable battery, or a combination of at least one capacitor and at least one rechargeable battery. Alternatively, a battery may be implanted in the patient for supplying electric energy to implanted electric energy consuming components of the apparatus, in addition to the supply of wireless energy.

Where the control device comprises an implantable control unit the electronic circuit thereof and the stimulation device may be directly powered with transformed wireless energy, or energy from either the implanted energy storage device or battery.

In accordance with a second main aspect of the invention, the wireless energy is directly used for the power of the stimulation device, i.e. the stimulation device is powered as the wireless energy is released from the external source of energy by the control device. In this case the term "directly" is used to mean, on one hand, that the stimulation device is promptly powered by using the released energy whiteout first storing the latter, on the other hand, that the released energy may be somewhat delayed, in the order of seconds, by for instance an energy stabiliser before being used for the power of the stimulation device. As a result, a very simple control of the stimulation device is achieved and there are only a few implanted components of the apparatus. For example, there is no implanted source of energy, such as a battery, nor any implanted complicated signal control system. This gives the advantage that the apparatus will be extremely reliable.

In accordance with a third main aspect of the invention, the source of energy comprises an implantable internal source of energy. Thus, when the internal source of energy is implanted in a patient the control device controls it from outside the patient's body to release energy. This solution is advantageous for sophisticated embodiments of the apparatus that have a relatively high consumption of energy that cannot be satisfied by direct supply of wireless energy.

The internal source of energy preferably comprises an electric source of energy, such as an accumulator or a battery.

In accordance with a fourth main aspect of the invention, the apparatus comprises a switch implanted in the patient for directly or indirectly switching the power of the stimulation device and an internal electric source of energy, such as a battery, implanted in the patient for supplying electric energy for the power of the stimulation device, wherein the switch directly or indirectly affects the supply of electric energy from the internal electric source of energy. This solution is advantageous for embodiments of the apparatus that have a relatively high consumption of energy that cannot be met by direct supply of wireless energy.

In a first particular embodiment in accordance with the fourth main aspect of the invention, the switch switches between an off mode, in which the internal electric source of energy is not in use, and an on mode, in which the internal electric source of energy supplies electric energy for the power of the stimulation device. In this case, the switch is conveniently operated by the wireless energy released from the external source of energy to switch between the on and off modes. The control device, preferably comprising a wireless remote control, may control the external source of energy to release the wireless energy. The advantage of this embodiment is that the lifetime of the implanted electric source of energy, such as a battery, can be significantly prolonged, since the implanted source of energy does not supply energy when the switch is in its off mode.

In a second particular embodiment in accordance with the fourth main aspect of the invention, the control device comprises a wireless remote control for controlling the internal electric source of energy. In this case, the switch is operable by the wireless energy from the external source of energy to switch between an off mode, in which the internal electric source of energy and remote control are not in use, and a standby mode, in which the remote control is permitted to control the internal electric source of energy to supply electric energy for the power of the stimulation device.

In a third particular embodiment in accordance with the fourth main aspect of the invention, the apparatus further comprises an energy transforming device to be implanted in the patient for transforming the wireless energy into storable energy, and an implantable energy storage device for storing the storable energy, wherein the switch is operable by energy from the implanted energy storage device to switch between an off mode, in which the internal electric source of energy is not in use, and an on mode, in which the internal electric source of energy supplies electric energy for the power of the stimulation device. In this case, the control device suitably comprises a wireless remote control for controlling the energy storage device to operate the switch.

An external data communicator may be provided outside the patient's body and an internal data communicator to be implanted in the patient may be provided for communicating with the external data communicator. The internal data communicator may feed data related to the patient, or related to the stimulation device, back to the external data communicator. Alternatively or in combination, the external data communicator may feed data to the internal data communicator. The internal data communicator may suitably feed data related to at least one physical signal of the patient.

Suitably, an implantable stabiliser, such as a capacitor, a rechargeable accumulator or the like, may be provided for stabilising the electric energy released by the control device. In addition, the control device may control the source of energy to release energy for a determined time period or in a determined number of energy pulses.

All of the above embodiments are preferably remote controlled. Thus, the control device advantageously comprises a wireless remote control transmitting at least one wireless control signal for controlling the stimulation device. With such a remote control it will be possible to adapt the function of the apparatus to the patient's need in a daily basis, which is beneficial with respect to the treatment of the patient.

The wireless remote control may be capable of obtaining information on the condition of the stimulation device and of controlling the stimulation device in response to the information. Also, The remote control may be capable of sending information related to the stimulation device from inside the patient's body to the outside thereof.

In a particular embodiment of the invention, the wireless remote control comprises at least one external signal transmitter or transceiver and at least one internal signal receiver or transceiver implantable in the patient. In another particular embodiment of the invention, the wireless remote control comprises at least one external signal receiver or transceiver and at least one internal signal transmitter or transceiver implantable in the patient.

The remote control may transmit a carrier signal for carrying the control signal, wherein the carrier signal is frequency, amplitude or frequency and amplitude modulated and is digital, analogue or digital and analogue. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analogue, and may comprise an electric or magnetic field. Suitably, the wireless remote control may transmit an electromagnetic carrier wave signal for carrying the digital or analogue control signal. For example, use of an analogue carrier wave signal carrying a digital control signal would give safe communication. The control signal may be transmitted in pulses by the wireless remote control.

The control device may be activated in a manual or non-manual manner to control the source of energy to release energy.

In the above-presented embodiments of the invention the released energy may comprise electric energy and an implantable capacitor having a capacity less than 0,1 $\mu$F may be provided for producing the above-mentioned train of energy pulses.

Generally, the wireless energy comprises a signal.

The apparatus may further comprise an implantable energy transforming device for transforming wireless energy, for example in the form of sound waves, directly or indirectly into electric energy, for the power of the stimulation device. More specifically, the energy transforming device may comprise a capacitor adapted to produce electric pulses from the transformed electric energy.

Generally, the stimulation device advantageously is embedded in a soft or gel-like material, such as a silicone material having hardness less than 20 Shore.

The stimulation device may comprise a band for application around the cardia, wherein the band has electric conductors for contacting the cardia sphincter. The electric conductors may comprise hooks to secure the conductors on the cardia.

All the above described various components may be combined in the different embodiments where applicable. Also the various functions described in connection with the above embodiments of the invention may be used in different applications, where applicable.

All the various ways of transferring energy and controlling the energy presented in the present specification may be practised by using all of the various components and solutions described.

The present invention also provides methods for treating heartburn and reflux disease.

Accordingly, in accordance with a first alternative method, there is provided a method of treating heartburn and reflux disease, comprising the steps of implanting an electric stimulation device in a patient, so that the stimulation device engages the cardia, providing an electric source of energy, and controlling the electric source of energy to power the stimulation device to electrically stimulate the cardia sphincter to increase the sphincter tonus, so that the cardia completely closes.

The first alternative method may also be performed laparascopically. Thus, there may be provided a laparascopic method of treating heartburn and reflux disease, comprising the steps of laparasopically implanting an electric stimulation device in a patient, so that the stimulation device engages the cardia, providing an electric source of energy, and controlling the electric source of energy to power the stimulation device to electrically stimulate the cardia sphincter to increase the sphincter tonus, so that the cardia completely closes.

In accordance with a second alternative method, there is provided a method of treating a patient having heartburn and reflux disease, comprising: (a) Surgically implanting in the patient an electric stimulation device engaging the cardia. (b) Providing a source of energy external to the patient's body. (c) Controlling the external source of energy from outside the patient's body to release wireless energy. And (d) using the released wireless energy in connection with the powering of the stimulation device.

The second alternative method may further comprise implanting an energy transforming device, controlling the external source of energy to release wireless energy, and transforming the wireless energy by the energy transforming device into energy different from the wireless energy for use in connection with the power of the stimulation device. This method may further comprise implanting a stabiliser in the patient for stabilising the energy transformed by the energy-transforming device.

The invention is described in more detail in the following with reference to the accompanying drawings, in which FIG. 1 is a schematic block diagram illustrating an embodiment of the heartburn and reflux disease apparatus of the invention, in which wireless energy is released from an external source of energy for use in the power of a stimulation device;

Referring to the drawing figures, like reference numerals designate identical or corresponding elements throughout the several figures.

Figure 1:
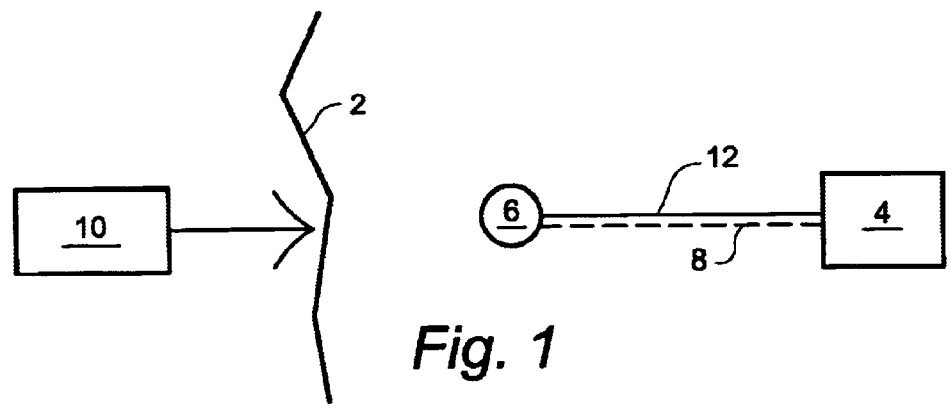

FIG. 1 schematically shows an embodiment of the heartburn and reflux disease apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body. The apparatus of FIG. 1 comprises an implanted electric stimulation device 4, which engages the patient's cardia sphincter to provide electric connection thereto. An implanted control unit 6 controls the stimulation device 4 via a control line 8. An external control unit 10 includes an external source of energy and a wireless remote control transmitting a control signal generated by the external source of energy. The control signal is received by a signal receiver incorporated in the implanted control unit 6, whereby the control unit 6 controls the implanted stimulation device 4 in response to the control signal. The implanted control unit 6 also uses electric energy drawn from the control signal for powering the stimulation device 4 via a power supply line 12.

Figure 2:
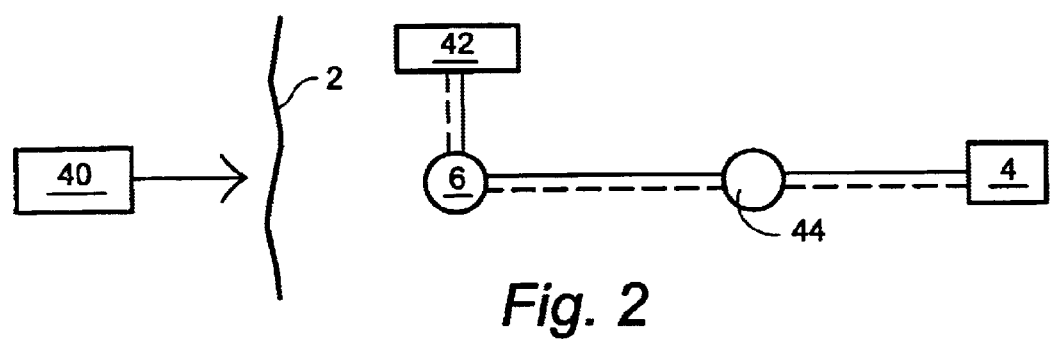
FIG. 2 is a schematic block diagram illustrating another embodiment of the invention, in which wireless energy is released from an internal source of energy.

FIG. 2 shows an embodiment of the invention identical to that of FIG. 1, except that an implanted internal electric source of energy in the form of a battery 42 is substituted for the external source of energy. Thus, an external control unit 40 without any source of energy is used in this embodiment. In response to a control signal from the external control unit 40 the implanted control unit 6 powers the stimulation device 4 with energy from the battery 42.

Figure 3:
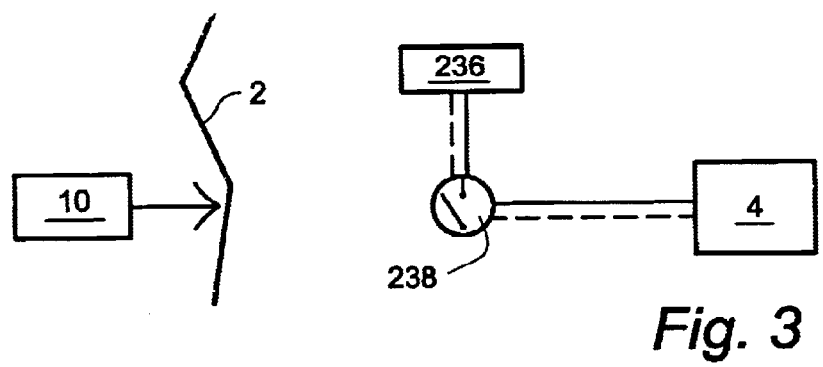
FIGS. 3 to 6 are schematic block diagrams illustrating four embodiments, respectively, of the invention, in which a switch is implanted in the patient for directly or indirectly switching the power of the stimulation device.

FIG. 3 shows an embodiment of the invention comprising the stimulation device 4, the external control unit 10, and an implanted source of energy 236 and an implanted switch 238. The switch 238 is operated by wireless energy released from the external source of energy of the external control unit 6 to switch between an off mode, in which the implanted source of energy 236 is not in use, and an on mode, in which the implanted source of energy 236 supplies energy for the power of the stimulation device 4.

Figure 4:
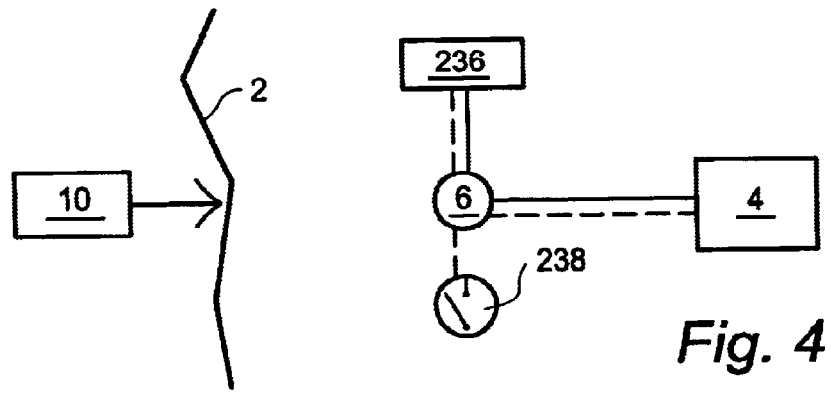

FIG. 4 shows an embodiment of the invention identical to that of FIG. 3, except that also the control unit 6 is implanted, in order to receive a control signal from the wireless remote control of the external control unit 10. The switch 238 is operated by the wireless energy from the external source of energy 10 to switch between an off mode, in which the implanted source of energy 236 and the wireless remote control of the external control unit 10 are not in use, i.e. the control unit 6 is not capable of receiving the control signal, and a standby mode, in which the wireless remote control is permitted to control the internal source of energy 236, via the implanted control unit 6, to supply energy for the power of the stimulation device 4.

Figure 5:
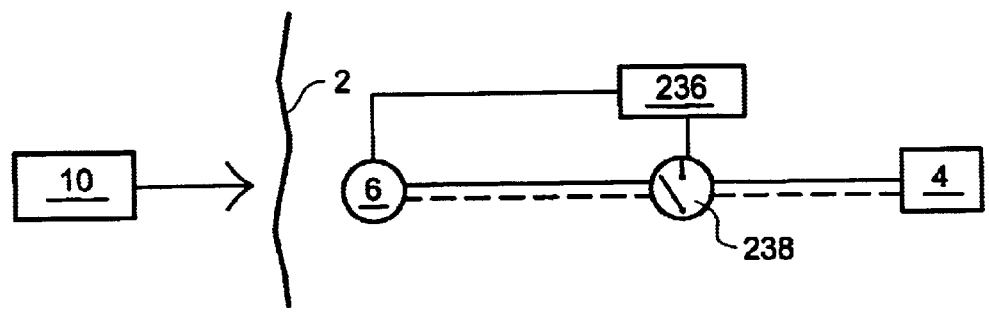

FIG. 5 shows an embodiment of the invention identical to that of FIG. 4, except that an energy transforming device for transforming the wireless energy into storable energy is incorporated in the implanted control unit 6 and that the implanted source of energy 236 is of a type that is capable of storing the storable energy. In this case, in response to a control signal from the external control unit 10, the implanted control unit 6 controls the switch 238 to switch from an off mode, in which the implanted source of energy 236 is not in use, to an on mode, in which the source of energy 36 supplies energy for the power of the stimulation device 4.

Figure 6:
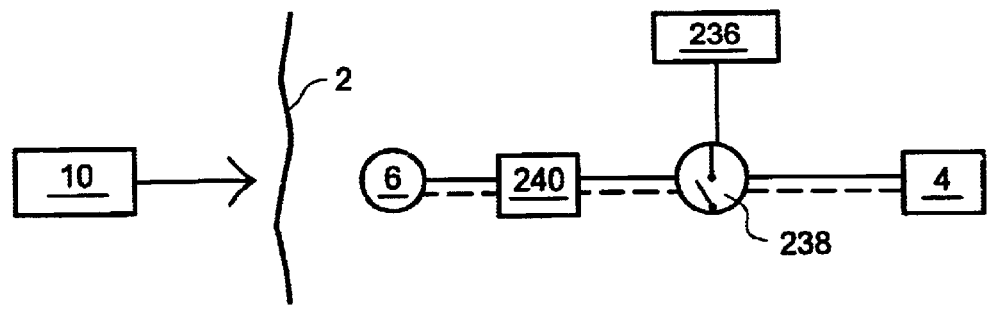

FIG. 6 shows an embodiment of the invention identical to that of FIG. 5, except that an energy storage device 240 also is implanted in the patient for storing the storable energy transformed from the wireless energy by the transforming device of the control unit 6. In this case, the implanted control unit 6 controls the energy storage device 240 to operate the switch 238 to switch between an off mode, in which the implanted source of energy 236 is not in use, and an on mode, in which the implanted source of energy 236 supplies energy for the power of the stimulation device 4.

Figure 7:
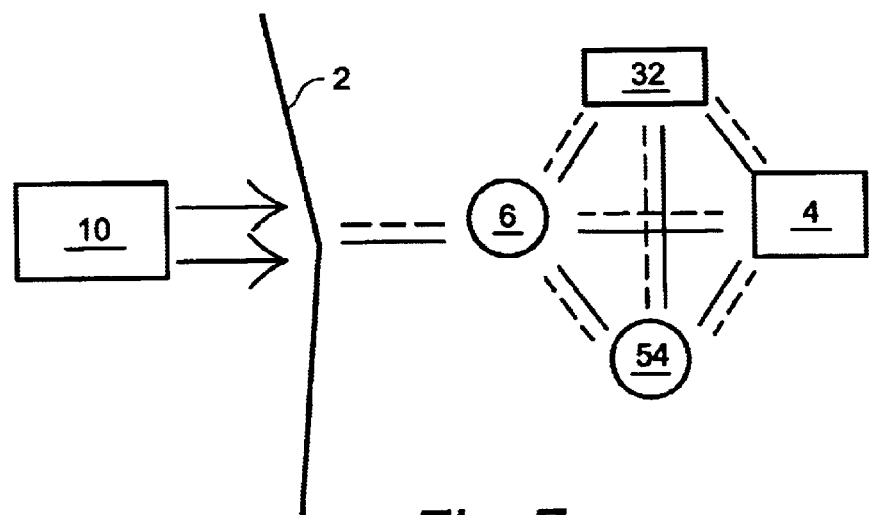
FIG. 7 is a schematic block diagram illustrating conceivable combinations of implantable components for achieving various communication options.

FIG. 7 schematically shows conceivable combinations of implanted components of the apparatus for achieving various communication possibilities. Basically, there are the implanted stimulation device 4, the implanted control unit 6 and the external control unit 10 including the external source of energy and the wireless remote control. As already described above the remote control transmits a control signal generated by the external source of energy, and the control signal is received by a signal receiver incorporated in the implanted control unit 6, whereby the control unit 6 controls the implanted stimulation device 4 in response to the control signal.

A sensor 54 may be implanted in the patient for sensing a physical parameter of the patient, such as the pressure in the esophagus. The control unit 6, or alternatively the external control unit 10, may control the stimulation device 4 in response to signals from the sensor 54. A transceiver may be combined with the sensor 54 for sending information on the sensed physical parameter to the external control unit 10. The wireless remote control of the external control unit 10 may comprise a signal transmitter or transceiver and the implanted control unit 6 may comprise a signal receiver or transceiver. Alternatively, the wireless remote control of the external control unit 10 may comprise a signal receiver or transceiver and the implanted control unit 6 may comprise a signal transmitter or transceiver. The above transceivers, transmitters and receivers may be used for sending information or data related to the stimulation device from inside the patient's body to the outside thereof. For example, the battery 32 may be equipped with a transceiver for sending information on the charge condition of the battery.

Those skilled in the art will realise that the above various embodiments according to FIGS. 1–6 could be combined in many different ways.

Figure 8:
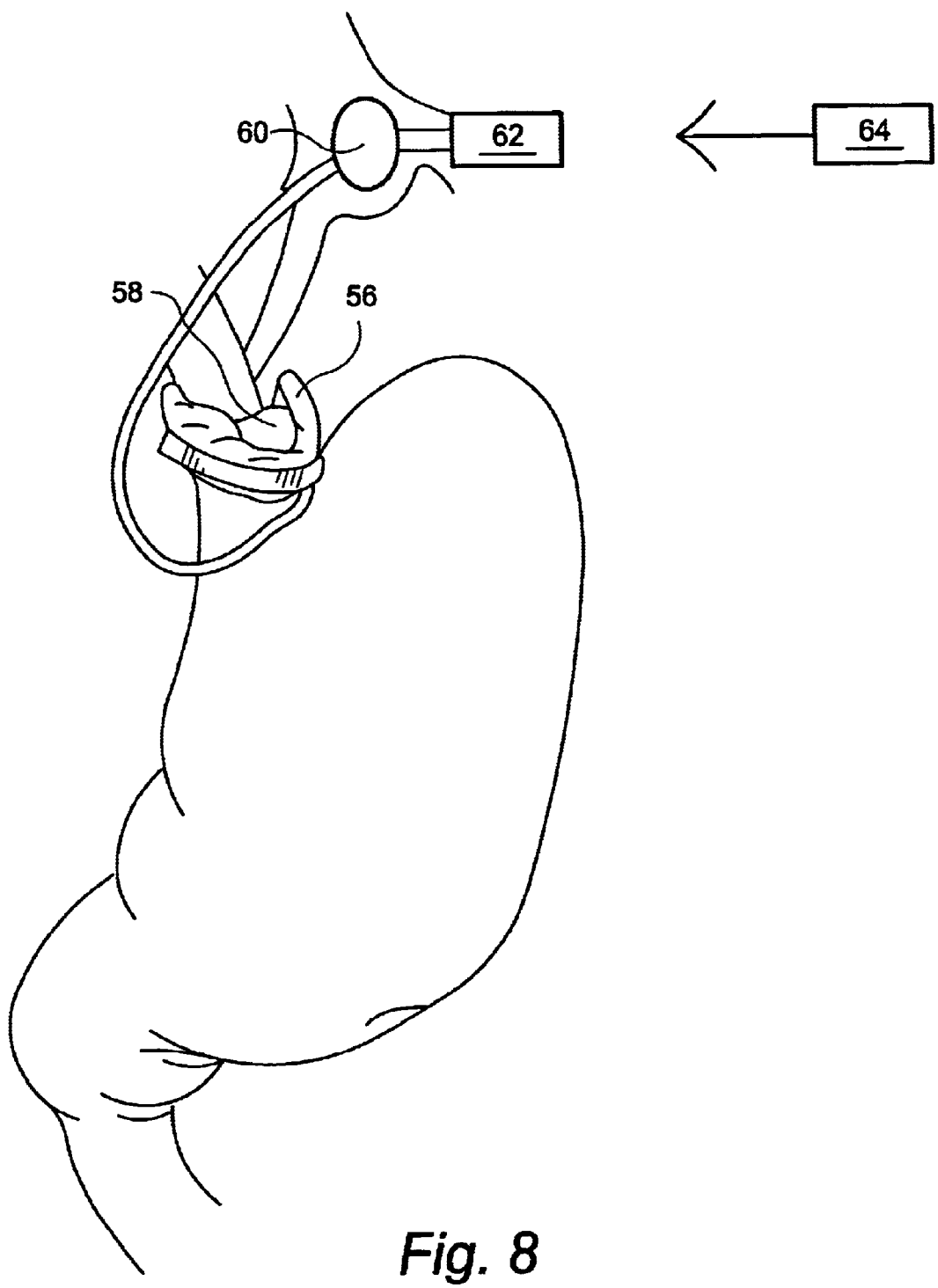
FIG. 8 illustrates the apparatus in accordance with the invention implanted in a patient.

FIG. 8 illustrates how any of the above-described embodiments of the heartburn and reflux disease treatment apparatus of the invention may be implanted in a patient. Thus, an assembly of the apparatus implanted in the patient comprises a stimulation device in the form of a band 56, which is wrapped around the cardia 58. The band 58 is provided with conductors that electrically contact the cardia sphincter and an operation device 60 for operating the stimulation device 56. An implanted control unit 60 is provided for controlling the supply of electricity to the band 56. There is an implanted energy transforming device 62 for transforming wireless energy into electric energy. The transforming device 62 also includes a signal receiver. An external control unit 64 includes a signal transmitter for transmitting a control signal to the signal receiver of the implanted transforming device 62. The transforming device 62 is capable of transforming signal energy from the control signal into electric energy for powering the stimulation device 60 and for energising other energy consuming implanted components of the apparatus.

Figure 9:
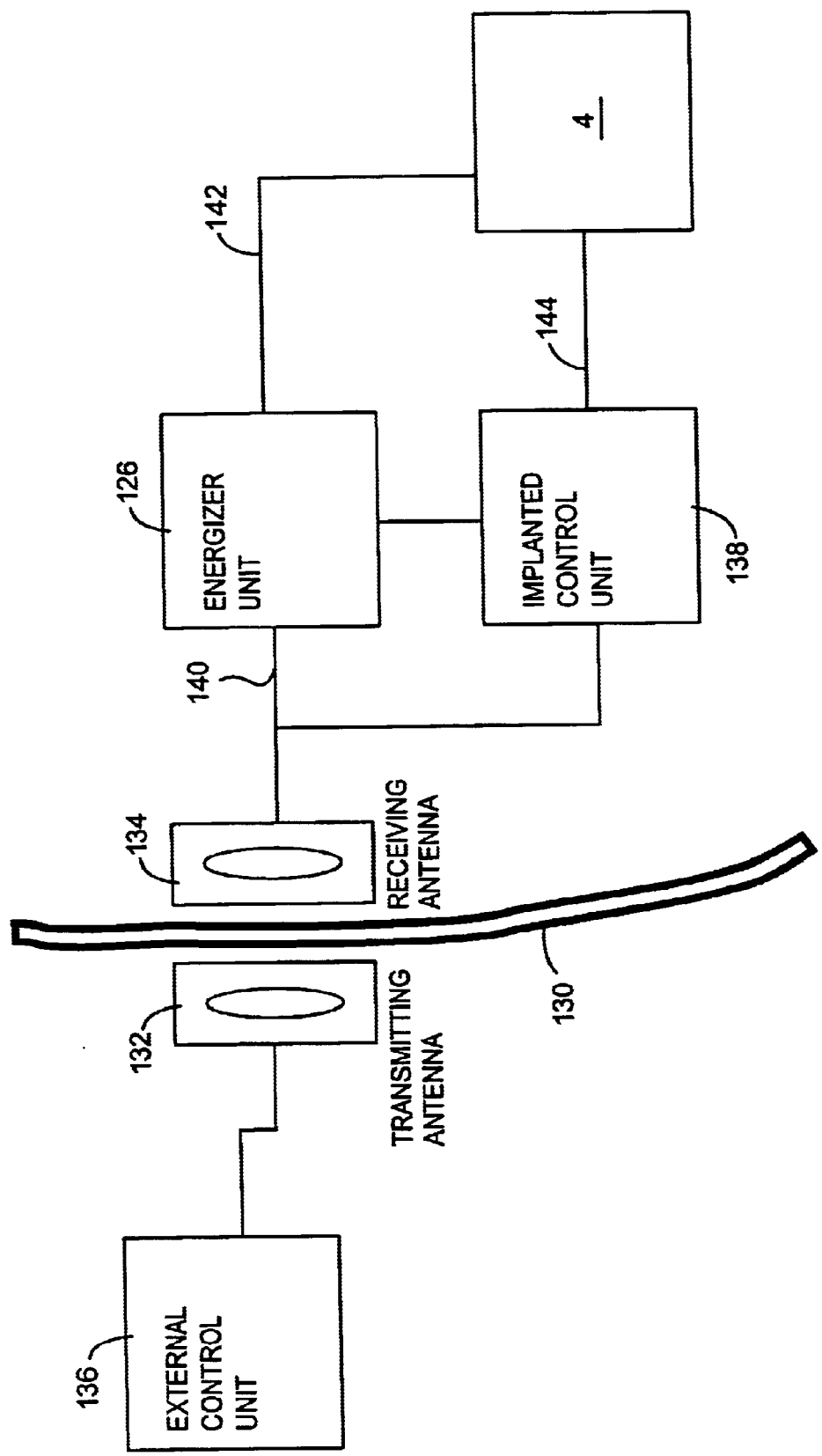
FIG. 9 is a block diagram illustrating remote control components of an embodiment of the invention.

FIG. 9 shows the basic parts of a wireless remote control Of the apparatus of the invention including an implanted electric stimulation device 4. In this case, the remote control is based on the transmission of electromagnetic wave signals, often of high frequencies in the order of 100 kHz–1 gHz, through the skin 130 of the patient. In FIG. 9, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1–100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132, 134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either power or not power the stimulation device. The microprocessor starts a command by applying a high frequency signal on the antenna 132. After a short time, when the signal has energised the implanted parts of the control system, commands are sent to power the stimulation device. The commands are sent as digital packets in the form illustrated below.

| Start pattern, | Command, | Count, | Checksum, |
|---|---|---|---|
| 8 bits | 8 bits | 8 bits | 8 bits |

The commands may be sent continuously during a rather long time period. When a new power or not power step is desired the Count byte is increased by one to allow the implanted control unit 138 to decode and understand that another step is demanded by the external control unit 136. If any part of the digital packet is erroneous, its content is simply ignored.

Through a line 140, an implanted energiser unit 126 draws energy from the high frequency electromagnetic wave signals received by the receiving antenna 134. The energiser unit 126 stores the energy in a power supply, such as a large capacitor, powers the control unit 138 and powers the electric stimulation device 4 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energiser unit 126 has sufficient energy stored, powers the stimulation device 4 via a line 144.

Alternatively, the energy stored in the power supply of the energiser unit may only be used for powering a switch, and the energy for powering the stimulation device 4 may be obtained from another implanted power source of relatively high capacity, for example a battery. In this case the switch is adapted to connect said battery to the control unit 138 in an on mode when the switch is powered by the power supply and to keep the battery disconnected from the control unit in a standby mode when the switch is not powered.

What is claimed is:

1. A heartburn and reflux disease treatment apparatus, comprising:
    an implantable electrical stimulation device adapted to engage with the cardia sphincter of a patient, who suffers from heartburn and reflux disease, and electrically stimulate the cardia sphincter to increase the sphincter tonus, so that the cardia completely closes,
    an electric source of energy, and
    a wireless remote control device controllable from outside the patient's body to control the electric source of energy to supply the stimulation device with electric energy, whenever the patient wants to during the day, when the stimulation device is implanted.

2. An apparatus according to claim 1, wherein the electric source of energy is adapted to provide a current through the electric conductors, and the control device is adapted to control the electric source of energy to release electric energy such that the intensity of the current through the electric conductors amounts to a predetermined value.

3. An apparatus according to claim 2, wherein the control device is adapted to control the electric source of energy to release electric energy in the form of an alternating current.

4. An apparatus according to claim 1, wherein the control device controls the stimulation device.

5. An apparatus according to claim 4, wherein the control device is adapted to control the stimulation device to vary the intensity of the electric stimulation of the cardia sphincter over time.

6. An apparatus according to claim 5, wherein the control device is controllable from outside the patient's body to control the stimulation device to change the intensity of the electric stimulation of the cardia sphincter so that the tonus of the cardia sphincter is changed.

7. An apparatus according to claim 4, wherein the control device comprises an internal control unit implantable in the patient for controlling the stimulation device.

8. An apparatus according to claim 7, wherein the internal control unit is programmable.

9. An apparatus according to claim 8, wherein the control device comprises an external control unit intended to be outside the patient's body, the internal control unit being programmable by the external control unit.

10. An apparatus according to claim 9, wherein the external control unit loads the internal control unit with data in accordance with a loading mode only authorised for a doctor.

11. An apparatus according to claim 9, wherein the external control unit controls the internal control unit in accordance with a doctor mode only authorised for a doctor.

12. An apparatus according to claim 9, wherein the external control unit controls the internal control unit in accordance with a patient mode permitted for the patient.

13. An apparatus according to claim 8, wherein the internal control unit is programmable for controlling the stimulation device over time.

14. An apparatus according to claim 13, wherein the internal control unit controls the stimulation device over time in accordance with an activity schedule program.

15. An apparatus according to claim 13, wherein the internal control unit comprises a microprocessor.

16. An apparatus according to claim 1, further comprising at least one implantable sensor for sensing at least one physical parameter of the patient.

17. An apparatus according to claim 16, wherein the sensor comprises a pressure sensor for directly or indirectly sensing as the physical parameter the pressure in the esophagus of the patient.

18. An apparatus according to claim 16, wherein the sensor senses as the physical parameter the contraction wave in the esophagus caused by the patient swallowing food.

19. An apparatus according to claim 18, wherein the electric stimulation device is adapted to cease the stimulation of the cardia sphincter in response to the sensor sensing the contraction wave in the patient's esophagus.

20. An apparatus according to claim 16, further comprising a control device adapted to control the stimulation device in response to signals from the sensor.

21. An apparatus according to claim 20, wherein the control device comprises an internal control unit implantable in the patient, the internal control unit controlling the stimulation device in response to signals from the sensor.

22. An apparatus according to claim 21, wherein the control device comprises an external control unit outside the patient's body, the external control unit controlling the stimulation device in response to signals from the sensor.

23. An apparatus according to claim 22, wherein the external control unit stores information on the physical parameter sensed by the sensor and is manually operated to control the stimulation device based on the stored information.

24. An apparatus according to claim 16, further comprising at least one implantable sender for sending information on the physical parameter sensed by the sensor.

25. An apparatus according to claim 16, wherein the sensor senses as the physical parameter when the patient is lying down, and the electric stimulation device is adapted to maintain the stimulation of the cardia sphincter in response to the sensor sensing that the patient is lying down.

26. An apparatus according to claim 1, wherein the source of energy is intended to be external to the patient's body when the stimulation device is implanted therein, and the control device is adapted to control the external source of energy to release wireless energy for use in connection with the power of the stimulation device.

27. An apparatus according to claim 26, further comprising an energy storage device implantable in the patient for storing the wireless energy released from the external source of energy.

28. An apparatus according to claim 27, wherein the energy storage device comprises an accumulator.

29. An apparatus according to claim 28, wherein the accumulator comprises an electric accumulator.

30. An apparatus according to claim 29, wherein the electric accumulator comprises at least one capacitor or at least one rechargeable battery, or a combination of at least one capacitor and at least one rechargeable battery.

31. An apparatus according to claim 26, wherein the control device is adapted to control the external source of energy to release wireless energy for direct use in connection with the power of the stimulation device.

32. An apparatus according to claim 31, further comprising an activatable source of energy implantable in the patient, wherein the implantable source of energy is activated by wireless energy released from the external source of energy, to supply energy which is used in connection with the power of the stimulation device.

33. An apparatus according to claim 31, wherein the control device is adapted to control the external source of energy to intermittently release wireless energy in the form of a train of energy pulses for direct use in connection with the power of the stimulation device.

34. An apparatus according to claim 33, wherein the control device is adapted to control the source of energy to release electric energy, and further comprising an implantable capacitor for producing the train of energy pulses from the released energy.

35. An apparatus according to claim 34, wherein the capacitor has a capacity less than 0,1 $\mu$F.

36. An apparatus according to claim 26, further comprising an implantable stabiliser for stabilising the energy released by the control device.

37. An apparatus according to claim 36, wherein the energy released by the control device comprises electric energy and the stabiliser comprises at least one capacitor.

38. An apparatus according to claim 31, wherein the wireless energy comprises electromagnetic waves excluding radio waves.

39. An apparatus according to claim 26, wherein the wireless energy comprises a signal.

40. An apparatus according to claim 26, further comprising an implantable energy transforming device for transforming wireless energy directly or indirectly into electric energy for the power of the stimulation device.

41. An apparatus according to claim 40, wherein the energy transforming device transforms the wireless energy in the form of sound waves into electric energy for the power of the stimulation device.

42. An apparatus according to claim 41, wherein the energy transforming device comprises a capacitor.

43. An apparatus according to claim 42, wherein the capacitor is adapted to produce electric pulses from the transformed electric energy.

44. An apparatus according to claim 1, further comprising a battery implantable in the patient for supplying electric energy to implantable electric energy consuming components of the apparatus.

45. An apparatus according to claim 1, wherein the source of energy comprises an implantable internal source of energy.

46. An apparatus according to claim 45, wherein the internal electric source of energy comprises at least one accumulator, at least one capacitor or at least one rechargeable battery, or a combination of at least one capacitor and at least one rechargeable battery.

47. An apparatus according to claim 1, further comprising a switch implantable in the patient for directly or indirectly switching the power of the stimulation device.

48. An apparatus according to claim 47, wherein the source of energy comprises an internal electric source of energy implantable in the patient for supplying electric energy to the stimulation device, and wherein the switch directly or indirectly affects the supply of electric energy from the internal electric source of energy.

49. An apparatus according to claim 48, wherein the switch switches between an "off" mode, in which the internal electric source of energy is not in use, and an "on" mode, in which the internal electric source of energy supplies electric energy to the stimulation device.

50. An apparatus according to claim 47, wherein the source of energy is intended to be external to the patient's body and adapted to release wireless energy for use in connection with the power of the stimulation device, and wherein the switch is operable by the wireless energy released from the external source of energy.

51. An apparatus according to claim 48, further comprising an external source of energy adapted to release wireless energy for use in connection with the power of the stimulation device, and an energy transforming device implantable in the patient for transforming the wireless energy into electric energy, which is stored by the internal electric source of energy.

52. An apparatus according to claim 48, wherein the control device comprises a wireless remote control for controlling the internal electric source of energy.

53. An apparatus according to claim 52, further comprising an external source of energy adapted to release wireless energy for use in connection with the power of the stimulation device, wherein the switch is operable by the wireless energy from the external source of energy to switch between an "off" mode, in which the internal electric source of energy and remote control are not in use, and a "standby" mode, in which the remote control is permitted to control the internal electric source of energy to supply electric energy for the operation of the stimulation device.

54. An apparatus according to claim 48, further comprising an external source of energy adapted to release wireless energy for use in connection with the power of the stimulation device, an energy transforming device implantable in the patient for transforming the wireless energy into storable energy and an energy storage device implantable in the patient for storing the storable energy.

55. An apparatus according to claim 54, wherein the switch is operable by energy from the implantable energy storage device to switch between an "off" mode, in which the internal electric source of energy is not in use, and an "on" mode, in which the internal electric source of energy supplies electric energy to the stimulation device.

56. An apparatus according to claim 55, wherein the control device controls the energy storage device to operate the switch.

57. An apparatus according to claim 56, wherein the control device comprises a wireless remote control.

58. An apparatus according to claim 50, wherein the control device controls the external source of energy to release the wireless energy.

59. An apparatus according to claim 58, wherein the switch switches from an "off" mode, in which the internal electric source of energy is not in use, to an "on" mode, in which the internal source of electric energy supplies energy to the stimulation device.

60. An apparatus according to claim 59, wherein the control device controls the switch to switch between the "on" and "off" modes.

61. An apparatus according to claim 60, wherein the control device comprises a wireless remote control.

62. An apparatus according to claim 61, further comprising an external data communicator intended to be outside the patient's body and an internal data communicator implantable in the patient for communicating with the external communicator, wherein the internal data communicator feeds data related to the patient back to the external data communicator or the external data communicator feeds data to the internal data communicator.

63. An apparatus according to claim 62, wherein the internal data communicator feeds data related to the stimulation device.

64. An apparatus according to claim 62, wherein the internal data communicator feeds data related to at least one physical signal of the patient.

65. An apparatus according to claim 1, wherein the control device controls the source of energy to release energy for a determined time period.

66. An apparatus according to claim 1, wherein the control device controls the source of energy to release energy in a determined number of energy pulses.

67. An apparatus according to claim 1, wherein the control device is adapted to control the source of energy to release energy in a non-invasive manner.

68. An apparatus according to claim 1, wherein the control device comprises a wireless remote control for transmitting at least one wireless control signal for controlling the stimulation device.

69. An apparatus according to claim 68, wherein the remote control is capable of obtaining information on the condition of the stimulation device when the stimulation device is implanted and to control the stimulation device in response to the information.

70. An apparatus according to claim 68, wherein the wireless remote control comprises at least one external signal transmitter or transceiver and at least one internal signal receiver or transceiver implantable in the patient.

71. An apparatus according to claim 68, wherein the wireless remote control comprises at least one external signal receiver or transceiver and at least one internal signal transmitter or transceiver implantable in the patient.

72. An apparatus according to claim 68, wherein the remote control transmits a carrier signal for carrying the control signal.

73. An apparatus according to claim 72, wherein the carrier signal is frequency, amplitude or frequency and amplitude modulated.

74. An apparatus according to claim 72, wherein the carrier signal is digital, analogue or digital and analogue.

75. An apparatus according to claim 72, wherein the control signal used with the carrier signal is frequency, amplitude or frequency and amplitude modulated.

76. An apparatus according to claim 68, wherein the control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

77. An apparatus according to claim 68, wherein the control signal comprises an electric, magnetic or electric and magnetic field.

78. An apparatus according to claim 68, wherein the control signal is digital, analogue or digital and analogue.

79. An apparatus according to claim 78, wherein the remote control transmits an electromagnetic carrier wave signal for carrying the digital or analogue control signal.

80. An apparatus according to claim 68, wherein the control signal is transmitted in pulses by the wireless remote control.

81. An apparatus according to claim 1, wherein the stimulation device is embedded in a soft or gel-like material.

82. An apparatus according to claim 1, wherein the stimulation device is embedded in a silicone material having hardness less than 20 Shore.

83. An apparatus according to claim 1, wherein the stimulation device comprises a band for application around the cardia, the band having electric conductors for engaging the cardia sphincter.

84. An apparatus according to claim 83, wherein the electric conductors comprise hooks to secure the conductors on the cardia.

85. An apparatus according to claim 84, wherein the hooks are inserted into the cardia.

86. A heartburn and reflux disease treatment apparatus comprising:
   an implantable electric stimulation device adapted to engage with the cardia sphincter of a patient, who suffers from heartburn and reflux disease, and electrically stimulate the cardia sphincter to increase the sphincter tonus, so that the cardia completely closes, and
   at least one implantable pressure sensor for directly or indirectly sensing the pressure in the esophagus of the patient.

87. An apparatus according to 86, comprising a control device adapted to control the stimulation device in response to signals from the sensor.

88. An apparatus according to claim 87, wherein the control device comprises an internal control unit implantable in the patient, the internal control unit controlling the stimulation device in response to signals from the sensor.

89. An apparatus according to claim 88, wherein the control device comprises an external control unit outside the patient's body, the external control unit controlling the stimulation device in response to signals from the sensor.

90. An apparatus according to claim 89, wherein the external control unit stores information on the pressure sensed by the sensor and is manually operated to control the stimulation device based on the stored information.

91. A heartburn and reflux disease treatment apparatus, comprising:
   an implantable electric stimulation device adapted to engage with the cardia sphincter of a patient, who suffers from heartburn and reflux disease, and electrically stimulate the cardia sphincter to increase the sphincter tonus, so that the cardia completely closes,
   a source of energy, and
   a control device controllable from outside the patient's body for controlling the source of energy to release energy for use in connection with the power of the stimulation device, when the stimulation device is implanted,
   wherein the control device includes an internal control unit implantable in the patient for controlling the stimulation device.

92. An apparatus according to claim 91, wherein the internal control unit is programmable.

93. An apparatus according to claim 92, wherein the control device comprises an external control unit intended to be outside the patient's body, the internal control unit being programmable by the external control unit.

94. An apparatus according to claim 92, wherein the internal control unit is programmable for controlling the stimulation device over time.

95. An apparatus according to claim 94, wherein the internal control unit controls the stimulation device over time in accordance with an activity schedule program.

96. An apparatus according to claim 94, wherein the internal control unit comprises a microprocessor.

97. An apparatus according to claim 93, wherein the external control unit loads the internal control unit with data in accordance with a loading mode only authorised for a doctor.

98. An apparatus according to claim 93, wherein the external control unit controls the internal control unit in accordance with a doctor mode only authorised for a doctor.

99. An apparatus according to claim 93, wherein the external control unit controls the internal control unit in accordance with a patient mode permitted for the patient.

100. A heartburn and reflux disease treatment apparatus, comprising:
   an implantable electric stimulation device adapted to engage with the cardia sphincter of a patient, who suffers from heartburn and reflux disease, and electrically stimulate the cardia sphincter to increase the sphincter tonus, so that the cardia completely closes,
   a source of energy, and
   a control device controllable from outside the patient's body for controlling the source of energy to release energy for use in connection with the power of the stimulation device, when the stimulation device is implanted,
   wherein the source of energy is intended to be external to the patient's body when the stimulation device is implanted therein, and the control device is adapted to control the external source of energy to release wireless energy for use in connection with the power of the stimulation device.

101. An apparatus according to claim 100, further comprising an energy storage device implantable in the patient for storing the wireless energy released from the external source of energy.

102. An apparatus according to claim 101, wherein the energy storage device comprises an accumulator.

103. An apparatus according to claim 102, wherein the accumulator comprises an electric accumulator.

104. An apparatus according to claim 103, wherein the electric accumulator comprises at least one capacitor or at least one rechargeable battery, or a combination of at least one capacitor and at least one rechargeable battery.

105. An apparatus according to claim 100, wherein the control device is adapted to control the external source of energy to release wireless energy for direct use in connection with the power of the stimulation device.

106. An apparatus according to claim 105, further comprising an activatable source of energy implantable in the patient, wherein the implantable source of energy is activated by wireless energy released from the external source of energy, to supply energy which is used in connection with the power of the stimulation device.

107. An apparatus according to claim 105, wherein the control device is adapted to control the external source of energy to intermittently release wireless energy in the form of a train of energy pulses for direct use in connection with the power of the stimulation device.

108. An apparatus according to claim 107, wherein the control device is adapted to control the source of energy to release electric energy, and further comprising an implantable capacitor for producing the train of energy pulses from the released energy.

109. An apparatus according to claim 108, wherein the capacitor has a capacity less than 0,1 $\mu$F.

110. An apparatus according to claim 100, further comprising an implantable stabiliser for stabilising the energy released by the control device.

111. An apparatus according to claim 110, wherein the energy released by the control device comprises electric energy and the stabiliser comprises at least one capacitor.

112. An apparatus according to claim 100, wherein the wireless energy comprises electromagnetic waves excluding radio waves.

113. An apparatus according to claim 100, wherein the wireless energy comprises a signal.

114. An apparatus according to claim 100, further comprising an implantable energy transforming device for transforming wireless energy directly or indirectly into electric energy for the power of the stimulation device.

115. An apparatus according to claim 114, wherein the energy transforming device transforms the wireless energy in the form of sound waves into electric energy for the power of the stimulation device.

116. An apparatus according to claim 115, wherein the energy transforming device transforms the wireless energy in the form of sound waves directly into electric energy.

117. An apparatus according to claim 115, wherein the energy transforming device comprises a capacitor.

118. An apparatus according to claim 117, wherein the capacitor is adapted to produce electric pulses from the transformed electric energy.

119. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, an internal electric source of energy implantable in the patient for supplying electric energy to the stimulation device, a wireless remote control for controlling the internal electric source of energy, a switch implantable in the patient for directly or indirectly switching the power of the stimulation device, and an external source of energy adapted to release wireless energy, wherein the switch is operable by the wireless energy from the external source of energy to switch between an "off" mode, in which the internal electric source of energy and remote control are not in use, and a "standby" mode, in which the remote control is permitted to control the internal electric source of energy to supply electric energy for the operation of the stimulation device.

120. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, an internal electric source of energy implantable in the patient for supplying electric energy to the stimulation device, a switch implantable in the patient for directly or indirectly switching the power of the stimulation device, and an external source of energy adapted to release wireless energy, and an energy transforming device implantable in the patient for transforming the wireless energy into storable energy and an energy storage device implantable in the patient for storing the storable energy.

121. An apparatus according to claim 120, wherein the switch is operable by energy from the implantable energy storage device to switch between an "off" mode, in which the internal electric source of energy is not in use, and an "on" mode, in which the internal electric source of energy supplies electric energy to the stimulation device.

122. An apparatus according to claim 121, wherein the control device controls the energy storage device to operate the switch.

123. An apparatus according to claim 122, wherein the control device comprises a wireless remote control.

124. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, an internal electric source of energy implantable in the patient for supplying electric energy to the stimulation device, a switch implantable in the patient for directly or indirectly switching the power of the stimulation device, and an external source of energy adapted to release wireless energy, and an energy transforming device implantable in the patient for transforming the wireless energy into electric energy, which is stored by the internal source of energy.

125. An apparatus according to claim 124, wherein the switch switches from an "off" mode, in which the internal electric source of energy is not in use, to an "on" mode, in which the internal source of electric energy supplies energy to the stimulation device.

126. An apparatus according to claim 125, wherein the control device controls the switch to switch between the "on" and "off" modes.

127. An apparatus according to claim 126, wherein the control device comprises a wireless remote control.

128. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, a source of energy, and a control device controllable from outside the patient's body for controlling the source of energy to release energy for use in connection with the power of the stimulation device, when the stimulation device is implanted, wherein the control device comprises a wireless remote control for transmitting at least one wireless control signal for controlling the stimulation device, the remote control being capable of obtaining information on the condition of the stimulation device when the stimulation device is implanted and to control the stimulation device in response to the information.

129. An apparatus according to claim 128, further comprising at least one implantable sensor for sensing the condition of the patient.

130. An apparatus according to claim 129, further comprising an internal control unit implantable in the patient, the internal control unit controlling the stimulation device in response to signals from the sensor.

131. An apparatus according to claim 129, wherein the remote control stores the information on the condition of the stimulation device sensed by the sensor and is manually operated to control the stimulation device based on the stored information.

132. An apparatus according to claim 128, wherein the source of energy is intended to be external to the patient's body when the stimulation device is implanted therein, and the control device is adapted to control the external source of energy to release wireless energy for use in connection with the power of the stimulation device.

133. An apparatus according to claim 132, further comprising an energy storage device implantable in the patient for storing the wireless energy released from the external source of energy.

134. An apparatus according to claim 133, wherein the energy storage device comprises an accumulator.

135. An apparatus according to claim 134, wherein the accumulator comprises an electric accumulator.

136. An apparatus according to claim 135, wherein the electric accumulator comprises at least one capacitor or at least one rechargeable battery, or a combination of at least one capacitor and at least one rechargeable battery.

137. An apparatus according to claim 132, wherein the control device is adapted to control the external source of energy to release wireless energy for direct use in connection with the power of the stimulation device.

138. An apparatus according to claim 137, further comprising an activatable source of energy implantable in the patient, wherein the implantable source of energy is activated by wireless energy released from the external source of energy, to supply energy which is used in connection with the power of the stimulation device.

139. An apparatus according to claim 137, wherein the control device is adapted to control the external source of energy to intermittently release wireless energy in the form of a train of energy pulses for direct use in connection with the power of the stimulation device.

140. An apparatus according to claim 139, wherein the control device is adapted to control the source of energy to release electric energy, and further comprising an implantable capacitor for producing the train of energy pulses from the released energy.

141. An apparatus according to claim 140, wherein the capacitor has a capacity less than 0,1 $\mu F$.

142. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, a source of energy, and a control device controllable from outside the patient's body for controlling the source of energy to release energy for use in connection with the power of the stimulation device, when the stimulation device is implanted, wherein the control device comprises a wireless remote control for transmitting at least one wireless control signal for controlling the stimulation device and a carrier signal for carrying the control signal.

143. An apparatus according to claim 142, wherein the carrier signal is frequency, amplitude or frequency and amplitude modulated.

144. An apparatus according to claim 142, wherein the carrier signal is digital, analogue or digital and analogue.

145. An apparatus according to claim 142, wherein the control signal used with the carrier signal is frequency, amplitude or frequency and amplitude modulated.

146. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, a source of energy, and a control device controllable from outside the patient's body for controlling the source of energy to release energy for use in connection with the power of the stimulation device, when the stimulation device is implanted, wherein the control device includes a wireless remote control for transmitting at least one wireless control signal for controlling the stimulation device, the wireless control signal including an electric, magnetic or electric and magnetic field.

147. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, a source of energy, and a control device controllable from outside the patient's body for controlling the source of energy to release energy for use in connection with the power of the stimulation device, when the stimulation device is implanted, wherein the control device includes a wireless remote control for transmitting at least one wireless control signal for controlling the stimulation device, the wireless control signal being transmitted in pulses by the wireless remote control.

148. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, wherein the stimulation device is embedded in a soft or gel-like material.

149. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, wherein the stimulation device is embedded in a silicone material having hardness less than 20 Shore.

150. A heartburn and reflux disease treatment apparatus, comprising:

an implantable electric stimulation device adapted to engage with the cardia sphincter of a patient, who suffers from heartburn and reflux disease, and electrically stimulate the cardia sphincter to increase the sphincter tonus, so that the cardia completely closes, wherein the stimulation device includes a band for application around the cardia, the band having electric conductors for engaging the cardia sphincter, the electric conductors including hooks to secure the conductors on the cardia.

151. An apparatus according to claim 150, wherein the hooks are inserted into the cardia.

* * * * *